United States Patent [19]
Petrow

[11] 3,988,447
[45] Oct. 26, 1976

[54] PHARMACEUTICAL PREPARATIONS
[75] Inventor: Vladimir Petrow, London, England
[73] Assignee: The British Drug Houses Ltd., London, England
[22] Filed: Oct. 15, 1963
[21] Appl. No.: 316,466

[52] U.S. Cl. .............................................. 424/243
[51] Int. Cl.$^2$ ....................................... A61K 31/56
[58] Field of Search ..................... 167/78 C, 78 S; 424/243

[56] References Cited
UNITED STATES PATENTS
3,087,862  4/1963  Penn .................................. 167/78

OTHER PUBLICATIONS

Liggins, New Zealand Medical Journal pp. 235 & 236, May 1963.

*Primary Examiner*—Jerome D. Goldberg
*Attorney, Agent, or Firm*—Bacon & Thomas

[57] ABSTRACT

The invention relates to pharmaceutical preparation containing a 17a-acyloxy-6-methyl-16-methylene-pregna-4,6-diene-3,20-dione compound as an active ingredient, and to the use of such preparations for the palliative treatment and control of certain types of neoplasmin conditions.

8 Claims, No Drawings

PHARMACEUTICAL PREPARATIONS

This invention relates to new pharmaceutical preparations containing a 17α-acyloxy-6-methyl-16-methylene-pregna-4,6-diene-3,20-dione compound as an active ingredient, and to the use of such preparations for the palliative treatment and control of certain types of neoplasmin conditions. The acyloxy dienes of the new preparation have the formula I set forth below:

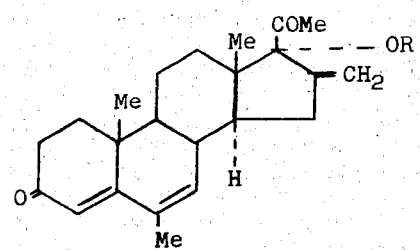

wherein R is an acyl radical of a hydrocarbon carboxylic acid of up to 6 carbon atoms, e.g., of the acetic, propionic, valeric and caproic acids. These compounds are prepared by the method set forth in copending application Ser. No. 41,256, filed July 7, 1960.

The treatment of certain neoplasmin conditions includes the treatment of endometrial carcinoma and leukemia in an afflicted host including animals and humans, although, of course, the utility of the products is not limited to the foregoing neoplasmic conditions.

The acetoxy derivative (I; R equals acetoxy) is the preferred compound. It has been found that 17α-acetoxy-6-methyl-16-methylene-6-dehydroprogesterone is particularly effective in obtaining palliative relief and remission of endometrial carcinomas. For example, otherwise untreatable cases of recurrent endometrial carcinomas in women patients have been treated successfully with this compound and worthwhile remissions and palliative relief obtained with no observed side effects. The compounds are especially suitable because, among the known progestogens, they are unique in being devoid of oestrogenic effects and have no anabolic or androgenic activity.

It has also been found from extensive experiments on test animals that the compounds have palliative and tumor growth control effects in the following neoplasmic conditions: Mammary Adenocarcinoma, Spontaneous Mesentery Lymphosarcoma, Acute Monocyclic Leukemia, Noll Line Mammary Adenocarcinoma, Spontaneous Leiomyosarcoma of Uterus, Spontaneous Lympho Sarcoma, Spontaneous Giant-Cell Sarcoma, Spontaneous Bronchiogenic Carcinoma, Acute Leukemia, Polymorphous Cell Sarcoma (induced), Spindle Cell Sarcoma of liver (induced), Malignant Hepatoma, Yoshida Sarcoma, Prostate Squamous Cell Carcinoma (induced) and Acute Lymphocyclic Leukemia.

The pharmaceutical preparations of the compounds having the Formula I may take the form of tablets, capsules, injections, elixirs, implantation pellets, pessary, ointments or creams.

Suitable daily doses of the compound comprise from about 1.0 mg to 100 mg, depending to some extent upon the weight of the animal or person treated. For example, for the treatment of endometrial carcinoma in the adult human, a satisfactory dosage is 20 mg daily of the active compound. This dosage may be continued as long as necessary in order to obtain effective relief and is completely free of side effects. However, smaller dosages may be used and up to 100 mg per day for periods of 12 months have been used, headaches being the only undesirable side effects observed. The compound is relatively non-toxic and, so, dose levels in excess of those quoted above may be used if necessary.

An example of a suitable preparation for oral administration in the form of yellow scored tablets each containing 10 mg of 17α-acetoxy-6-methyl-16-methylene-pregna-4,6-diene-3,20-dione is given below:

EXAMPLE 1

| | |
|---|---|
| 17α-Acetoxy-6-methyl-16-methylenepregna-4,6-diene-3,20-dione | 10 mg. |
| Lactose | 99 mg. |
| Starch | 13 mg. |
| Tartrazine lake | 0.5 mg. |
| Starch paste, 10 per cent w/w | a sufficient quantity |
| Magnesium stearate | 1.3 mg. |
| Starch, sufficient to produce | 129.6 mg. |

The first four ingredients are thoroughly mixed to give a uniform yellow color and granulated with a suitable quantity of 10 per cent starch paste, followed by tray drying at 50° C. The resultant granules are processed through a 20 mesh sieve and the lubricant (magnesium stearate) added, together with sufficient starch to produce the required weight. After thorough mixing, tablets each weighing 129.6 mg. are compressed from the mixture, using punches of convenient diameter and suitably embossed to provide a break-line.

Tablets made in accordance with Example 1 were administered to an elderly woman patient who had unsuccessfully undergone radium treatment two years previously for endometrial carcinoma. Histological examination of the patient showed a well-differentiated adenocarcinoma of the endometrial type displaying an adenopapillary pattern with occasional areas of squamous metaplasia. The patient was placed on a daily dosage of the composition of Example 1 which provided 20 mg. of the active component, 6-methyl-16-methylene-6-dehydro-17α-acetoxy progesterone per day. The response to this treatment was assessed by further curettage after several months. On this occasion, it proved difficult to obtain biopsy material; the uterine cavity and cervical canal being smooth and firm. The pathologist reported that sections were lacking the aggressive hyperchromatic appearance of cancer, the cells having the staining appearance of normal tissue nuclei, quiescent, normochromic and relatively smaller. No observable mitoses. The patient was readmitted for investigation after about six months. The pathological report stated that the sections showed quiescent tissue not recognizable as tumor tissue. On further checkup the patient remained well. At no times were there any side effects from the treatment.

EXAMPLE 2

The composition in parenteral injection form was tested in an animal test program utilizing rats as the test animals. The test procedure was as follows:

An aqueous suspending medium containing 0.9% sodium chloride, 0.4% polysorbate 80, 0.5% carboxymethyl cellulose and 0.9% benzyl alcohol, was prepared. The compound 17α-acetoxy-6-methyl-16-methylene-6-dehydroprogesterone was dispersed into a portion of the suspending medium by grinding. Portions of this suspension were diluted to provide a series of suspensions having different dosage levels of active compound.

A number of adult intact rats of inbred laboratory strains weighing approximately 200 grams each were selected for the tests.

On the first day of the testing schedule all of the animals were implanted either with grafts of tumor tissue or in some cases, as with some of the leukemias, spleen suspensions were used. The transplantation was accomplished by established laboratory procedure, from laboratory animals of the same strain having tumors which occurred spontaneously or which were induced by hydrocarbons, azo dyes or Taenia larvae in the inbred rats of the colony. The neoplasms were inoculated subcutaneously with a 13-gauge trocar on the right side or bilaterally, the grafts ranging from 2 to 10 mg. in size depending on the tumor system under test.

On the second day, the animals were randomized into control and test groups and individually weighed. One sex was always used for each group of test and control animals and each group consisted of eight to 10 animals. The proper dilutions of the injection composition were prepared and the first dose was administered. The composition was administered once daily, subcutaneously, on a mg./kg. of body weight basis in an 0.2 ml. dose until the end of the test period. The control animals were similarly inoculated with an 0.2 ml. dose of the suspending vehicle. Injections were made alternately in the right or left flank of all rats at a distance from the site of inoculation of the neoplasm. The number of injections were determined for the various tumor systems on the basis of past experience with the survival time of the individual tumor System in untreated animals. In the case of very slow growing systems the injections were usually given from 20 to 30 days.

The rats were weighed weekly; the tumors were measured as soon as they were palpable and weekly thereafter. The three largest diameters were recorded in centimeters and an average diameter was obtained for comparison. After completion of the injection schedule the rats were observed until death for further growth of the tumors and average survival time. At necropsy a representative section of each tumor, the axillary and mediastinal lymph nodes, 4 sections of the lungs, and a section of the liver, sleen, and kidney were preserved for microscopic examination.

Results of the tests are as follows:

| | | |
|---|---|---|
| Leukemia | | |
| 10.6 mg/kg/day | Good activity (59%)* | Increased S.T.° |
| 26.5 mg/kg/day | Good activity (50%) | Increased S.T. |
| Acute Monocytic Leukemia | | |
| 1 mg/kg/day | slight activity | Increased S.T. |
| 25.0 mg/kg/day | Good activity (49% & 58%) | Increased S.T. |
| 34.0 mg/kg/day | Very good activity (1%) | Increased S.T. |
| Malignant Hepatoma | | |
| 40.0 mg/kg/day | Some activity | |
| Spontaneous Giant-Cell Sarcoma | | |
| 30.0 mg/kg/day | Quite good activity (68%) | Increased S.T. |
| 18.0 mg/kg/day | Good activity (37%) | Increased S.T. |
| Spontaneous Leiomyosarcoma of Uterus | | |
| 20.0 mg/kg/day | Some activity | Increased S.T. |
| 21.0 mg/kg/day | Tumor growth <control | Increased S.T. |
| 26.8 mg/kg/day | Slight activity | Increased S.T. |
| Prostate Squamous Cell Carcinoma | | |
| 10.0 mg/kg/day | Some activity | Increased S.T. |
| 25.0 mg/kg/day | Some activity (74%) | Increased S.T. |
| Mammary Adenocarcinoma | | |
| 6.25 mg/kg/day | Some activity | |
| 12.5 mg/kg/day | | |
| 25.0 mg/kg/day | | |
| Acute Leukemia | | |
| 40.0 mg/kg/day | Increased survival time | |
| 12.5 mg/kg/day | | |
| 27.5 mg/kg/day | | |
| Acute Lymphocytic Leukemia | | |
| 25.0 mg/kg/day | Good activity (51%) | Increased S.T. |
| Spontaneous Lymphosarcoma | | |
| 40.0 mg/kg/day | Some activity (74%) | Increased S.T. |
| Spontaneous Mesentery Lymphosarcoma | | |
| 40.0 mg/kg/day | Some activity | Increased S.T. |
| Huggins Mammary Fibroadenoma | | |
| 1.0 mg/kg/day | Tumor weight <control | |

*Test compound/control with respect to tumor growth
°S.T. = Survival time

From the foregoing it will be seen that the compositions set forth are quite effective for treatment of endometrial carcinoma in humans and for a number of neoplasmin conditions, including leukemia in animals.

I claim:

1. A method for palliative treatment of endometrial carcinoma comprising: administering to the human female afflicted with said endometrial carcinoma a daily dosage of from about 1.0 to about 100 mg. of a compound having the formula wherein R is an acyl group of hydrocarbon carboxylic acid having up to six carbon atoms.

2. The method of claim 1 wherein said compound is orally administered in a pharmaceutically-acceptable carrier.

3. The method of claim 1 wherein said compound is injected parenterally.

4. The method of claim 1 wherein said compound is 17α-acetoxy-6-methyl-16-methylenepregna-4,6-diene-3,20-dione.

5. A method for the palliative treatment of endometrial carcinoma comprising orally administering to a human female afflicted with said endometrial carcinoma a daily dosage of from about 1.0 to about 100 mg of 17α-acetoxy-6-methyl-16-methylenepregna-4,6-diene-3,20-dione.

6. A method for palliative treatment of acute monocytic leukemia in animals comprising: administering to the animal afflicted with said leukemia a daily dosage of from about 1 to 40 mg./kg of body weight of 17α-acyloxy-6-methyl-16-methylenepregna-4,6-diene-3,20-dione wherein the acyl group is derived from a hydrocarbon carboxylic acid having up to six carbon atoms.

7. A method for palliative treatment of prostate squamous cell carcinoma in animals comprising: administering to the animal afflicted with said prostate squamous cell carcinoma a daily dosage of from about 1 to 40 mg./kg. of body weight of 17α-acyloxy-6-methyl-16-methylenepregna-4,6-diene-3,20-dione wherein the acyl group is derived from a hydrocarbon carboxylic acid having up to six carbon atoms.

8. A method for palliative treatment of mammary adenocarcinoma in animals comprising: administering to the animal afflicted with said mammary adenocarcinoma a daily dosage of from about 1 to 40 mg./kg. of body weight of 17α-acyloxy-6-methyl-16-methylenepregna-4,6-diene-3,20-dione wherein the acyl group is derived from a hydrocarbon carboxylic acid having up to six carbon atoms.

* * * * *